| United States Patent [19] | | [11] 3,960,671 |
|---|---|---|
| Clovis et al. | | [45] June 1, 1976 |

[54] QUINONES AS CORROSION INHIBITOR IN DISTILLING ALKANOIC ACIDS

[75] Inventors: James S. Clovis, Morrisville; Jerome Dohling, Huntingdon Valley, both of Pa.

[73] Assignee: Rohm and Haas Company, Philadelphia, Pa.

[22] Filed: June 17, 1974

[21] Appl. No.: 480,063

[52] U.S. Cl. ................................ 203/7; 203/57; 203/86; 260/540; 260/541; 260/542
[51] Int. Cl.$^2$ .......................................... C23F 14/02
[58] Field of Search ............... 203/7, 8, 6, 57, 38, 203/86; 159/DIG. 13, 20; 252/393; 134/11, 12; 260/540, 541, 542

[56] References Cited
UNITED STATES PATENTS

| 2,907,699 | 10/1959 | Millidge et al. ............................ 203/7 |
|---|---|---|
| 3,084,109 | 4/1963 | Reid Ure et al. ........................ 203/37 |
| 3,277,120 | 10/1966 | Fullhart, Jr. et al. ............... 252/393 |
| 3,413,237 | 11/1968 | Foroulis ...................................... 203/7 |
| 3,490,997 | 1/1970 | Burney et al. ........................... 203/7 |
| 3,551,349 | 12/1970 | Kallfass ................................. 252/393 |
| 3,781,193 | 12/1973 | Sennewald et al. ...................... 203/8 |
| 3,794,567 | 2/1974 | Otsuki et al. ............................. 203/8 |
| 3,843,547 | 10/1974 | Kaufman et al. .................... 252/392 |

OTHER PUBLICATIONS

C. R. Noller, *Chemistry of Organic Compounds*, 1951, pp. 506–509.

*Primary Examiner*—Curtis P. Ribando

[57] ABSTRACT

A process is disclosed for distilling corrosive carboxylic acids free of olefinic unsaturation in distillation apparatus constructed of corrodible metal, which includes the steps of introducing a crude dilute solution of such a corrosive acid into the distillation zone, distilling in the presence of an effective amount of p-benzoquinone or of 1,4-naphthoquinone, and recovering the concentrated corrosive acid outside the distillation zone. The amount of p-benzoquinone or of 1,4-naphthoquinone is such as to effectively prevent or reduce to acceptable limits the corrosion of the metal distillation apparatus by such acids, and also to permit this distillation process to be effectuated at those high acid vapor temperatures which otherwise would not be feasible because of the heightened degree of corrosiveness exhibited by the acids at such temperatures.

21 Claims, No Drawings

QUINONES AS CORROSION INHIBITOR IN DISTILLING ALKANOIC ACIDS

This invention concerns the use of p-benzoquinone or 1,4-naphthoquinone as a corrosion inhibitor in the distillation of corrosive carboxylic acids, free of olefinic unsaturation, in corrodible distillation apparatus, such that distillation of dilute crude solutions of such acids can be carried out at a wide range of vapor temperatures, with little or no corrosion of the metallic apparatus, especially at those high temperatures where corrosion is most severe.

It is well-known that the lower chain saturated alkanoic acids are corrosive to a wide range of metals and alloys. Lower chain saturated alkanoic acids such as those of the general formula:

R—COOH where R = H, $H(CH_2)_n$ and $n = 0$ to 3, or

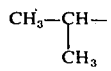

exert a direct corrosive effect on unprotected metals. This problem is most acute in those industries which prepare or purify dilute solutions of the aforementioned acids by distillation in essentially corrosion-resistant metallic distillation apparatus. While many alloys may theoretically be used, commercial advantage dictates the range of alloys that are acceptable on the basis of cost and useful life. The preferred alloys are the austenitic stainless steels which are iron-based alloys containing both chromium and nickel as the main alloying elements. The "work-horse" austenitic stainless steels of the chemical process industry are the so-called Type 18-8, so named because of their approximate chromium-nickel content, respectively 16–20% chromium and 8–15% nickel. These alloys break down into two general groups, the Type 304 and the Type 316, the former including stainless steels 304, 304L, 321 and 347; the latter stainless steels, 316, 316L, 316Cb (318) and 317. The nominal composition of each alloy is as follows, with the remainder being iron and residual elements:

|          | % C(max) | % Cr  | % Ni  | % Mo | % Cb/Ta | % Ti       |
|----------|----------|-------|-------|------|---------|------------|
| SS-304   | 0.08     | 18–20 | 8–12  | —    | —       | —          |
| SS-304L  | 0.03     | 18–20 | 8–12  | —    | —       | —          |
| SS-321   | 0.08     | 17–19 | 9–12  | —    | —       | 5 × C      |
| SS-347   | 0.08     | 17–19 | 9–13  | —    | 10 × C  | —          |
| SS-316   | 0.08     | 16–18 | 10–14 | 2–3  | —       | —          |
| SS-316L  | 0.03     | 16–18 | 10–14 | 2–3  | —       | —          |
| SS-316Cb | 0.08     | 16–18 | 10–14 | 2–3  | 10 × C  | —          |
| SS-317   | 0.08     | 18–20 | 11–15 | 3–4  | —       | —          |

Each of the above elements contributes in a specific way to the metallurgical structure and the corrosion resistance of the alloy, and these roles can be summarized as follows:

Carbon is an important constituent in austenitic stainless steel. Its importance, however, lies in the undesirable influence it has upon these alloys. When austenitic stainless steel is heated to and subsequently held within the range of 800°–1600°F the carbon tends to migrate from solid solution to the grain boundaries. Here it combines with chromium, forming a complex chromium carbide, $Cr_{23}C_6$, thus depleting the adjacent area of chromium to the point where corrosion resistance is impaired. This reaction occurs particularly with austenitic stainless steels containing > 0.03% carbon. Certain environments normally resisted by properly fabricated austenitic stainless steel induce corrosion, called intergranular attack. Carbon does not behave entirely as a malefactor since it is an important strengthening agent.

Chromium is a ferrite (alpha) former and thus tends to suppress the ferrite-to-austenite (alpha-to-gamma) transformation. This element is th basic agent for imparting corrosion protection. Its contribution apparently arises from its ability to form a microscopically thin layer of a chromium oxide complex over the entire surface of the metal. The alloy sans nickel (commonly called ferritic stainless steel) exhibits excellent resistance to oxidizing media and alkalies.

Nickel promotes formation and supports stability of austenite, i.e., it is a gamma former. In this condition, the alloy (chromium-nickel-carbon-iron) is face-centered cubic (FCC) in grain structure, is non-magnetic, and cannot be hardened via heat treatment. Nickel aids weldability, promotes ductility, and permits work-hardening. With regard to affect on corrosion resistance, nickel enhances the protective qualities of the aforementioned chromium oxide film.

Molybdenum has the same effect as chromium with regard to the alloy structure. It tends to increase the ferrite content. Molybdenum augments corrosion resistance of Type 304 to various reducing media. In other words, molybdenum facilitates the formation of a passive oxide film composed of both chromium and molybdenum. This oxide film is more stable than is the chromium oxide film and in this respect supports resistance to pitting attack such as occurs during exposure of Type 304 to sulfides, sulfates, phosphates, acetates, and their respective acids, as well as the chlorides and fatty acids. The addition of molybdenum, however, is deleterious when the environment is strongly oxidizing or is a strong alkali. This deterioration is apparently due to the presence of silicon, a residual element in the alloy makeup.

The primary function of niobium (columbium) is to thwart carbon in its effort to impoverish grain boundaries of chromium. Since carbon has a greater affinity for niobium than for chromium, the stable compound, niobium carbide, forms preferentially during stabilizing heat treatment, thus immobilizing the carbon and preventing chromium depletion. Niobium also serves to preserve mechanical strength at elevated temperatures.

Tantalum occurs in the same ore with niobium and apparently behaves in much the same way as does niobium.

Titanium plays the same role as does niobium. Regarding stabilization procedure, there are a number of points of superiority of Cb/Ta over Ti. Titanium combines much more avidly with oxygen than does Cb/Ta and is therefore more easily lost during welding. At elevated temperatures, columbium carbide appears to be more stable than its titanium counterpart. The Cb/Ta alloy, SS-347, is distinctly superior to the titanium system, SS-321, under strongly oxidizing conditions, although there is some evidence to indicate that SS-321 has the greater resistance to sulfates and sulfuric acid.

The normal condition of austenitic stainless steel is said to be passive, i.e. possesses a uniform oxide surface film which is primarily responsible for the good corrosion resistance. Conversely, the same alloy without the oxide film is said to be active. The range of solutions in which passivity takes place is a very broad one, yet, with many solutions there is a point, as the conditions become more severe, where a slight change in some conditions — increase in temperature, decrease in oxidizer or change in concentration — throws the metal from a state of passivity to one of activity. In general, these alloys in the active condition are rapidly corroded, in the passive condition virtually unattacked or relatively slowly attacked. The passivity-activity boundary, shifting often with delicate changes in exposure conditions, becomes in a sense the limit of usefulness of the alloy.

The effects of acids on austenitic steels is dependent on whether the acidity of the solution or the oxidizing capacity gains the upper hand. Most acid solutions at room temperature carry a moderate concentration of dissolved oxygen from the air. This is sufficient to provide passivity to metals in contact with most acid solutions that do not have a very high hydrogen-ion concentration. Acting together with oxidizing capacity and acid strength are a number of other factors that determine the passive-active boundary. These are: the aforementioned chromium, nickel, molybdenum and carbon content, and heat treatment. All of these factors are dependent on each other in their influence and it is for this reason that the boundary is not always readily anticipated. It is possible to outline fairly accurately, the behavior of Type 18-8 stainless steels (includes 304, 304L and 316) that have been properly heat treated:

a. Acid solutions of high hydrogen-ion concentration are resisted only if the oxidizing capacity of the solution is strong. $HNO_3$, 1–15% concentration in water, is an example of an acid that has sufficiently high oxidizing capacity to take care of the high hydrogen-ion concentration.

b. Acid solutions of intermediate hydrogen-ion concentration are well resisted so long as the oxidizing capacity is at least moderate. The dissolved oxygen normally present in a solution is often sufficient for passivity in such media as acetic acid. On the other hand, these solutions in the absence of dissolved oxygen are likely to be corrosive particularly under conditions of high acid concentration and at boiling temperatures.

c. When oxidizing capacity is insufficient to maintain passivity, corrosion of the metal can initiate. It is important to note that under conditions at the active-passive boundary corrosion may be extremely severe or almost completely absent, depending on whether the passivating effect of the oxidizing capacity has the upper hand or not.

d. If corrosion initiates, two forms of attack are possible: (1) uniform corrosion, and (2) localized attack, e.g., pitting. Uniform corrosion is essentially a result of the protective film being alternately dissolved and replenished in an increment of time. The rapidity and/or degree of refurbishment is a function of either the oxidizing capacity of the environment or the nature of the protective film. Pitting is characteristic of the passive metals and alloys and of metals and alloys in insufficiently inhibited environments. In the former case, local breakdown of passivity due to some inhomogeneity of the passive metal surface produces a "passive-active" cell of large potential differences. The cathodic area of the passive metal is depolarized, leaving voids in the oxide film that have a low hydrogen-ion over-voltage, allowing the cathodic reaction to proceed with elimination of hydrogen and consequent pitting at the small anodic site of the metal. This effect is especially pronounced at higher temperatures and may be due to the presence of hydrated molecules which greatly influence hydrogen over-voltage. Type 304 and 316 in a condition with less than the normal oxide film thickness required for protection will eventually exhibit pitting at weak points in the film. Hence, the rate of metal dissolution (uniform corrosion) versus local attack (pitting) is a function of the nature of the oxide film.

e. Elevated temperatures shift the active-passive border line in such a direction that a good many of the conditions that produce passivity at room temperature cause rapid corrosion at elevated temperatures. An important reason for this is the lowering of dissolved oxygen content by rising temperatures. Boiling solutions of acetic acid are extremely corrosive to SS-304, and may be eventually corrosive to SS-316.

Organic acids are non-oxidizing systems. Corrosion by these acids can be quite aggressive with formic acid being the most corrosive, with this corrosive nature decreasing with increase in the molecular weight. Another important factor is the temperature to which the acid-metal system is elevated. The lower molecular weight acids are more corrosive at high temperatures (at or near their boiling points) than are the high molecular weight acids.

The corrosive organic acids are generally thought to corrode by dissolving the oxide film and attacking the activated non-uniform surface of the alloy. Film repair is from oxygen present in the media. If the system contains either insufficient oxygen for film repair or no oxygen, the metal becomes susceptible to severe corrosion. These low oxygen conditions are well exemplified by the distillation process, where dilute solutions of the corrosive acids are purified in a system that is essentially closed to the ingress of air or an oxygen-containing gas. It is a situation where the high temperatures, and low oxygen levels combine to provide a system that is highly conducive to metallic corrosion.

In actual commercial practice, production of concentrated pure corrosive alkanoic acids is beset by a number of production problems. The manufacture of commercial and glacial acetic acid, as discussed in Kirk-Othmer "Encyclopedia Of Chemical Technology", 2nd edition, volume 8, pp. 397–400, is a typical example. The high reflux ratio necessary, with the concomitant high heat costs and excessive high column diameter, has generally precluded the use of simple rectification of dilute acetic acid solutions. One commercial process involves a series of organic solvent extractions of the dilute solution, followed by several azeotropic distillations, and finally an extractive distillation of the resulting more concentrated aqueous solution of acetic acid, often at reduced pressures so as to lower distillation temperatures in order to reduce corrosion by high temperature vapors. Added to these already costly processes is the problem of high cost of relatively corrosion-resistant alloys for construction of the distillation equipment and the eventual corrosion that occurs over a period of normal equipment usage.

The high alloys with relatively large percentages of nickel, notably Hastelloy B and C, are suitable for service at all concentrations of acetic acid and at all temperatures. But high cost and difficult fabrication limit their use. The use of less expensive alloys, however, raises the problem of corrosion. Commercial crude dilute acetic acid solutions may contain formic acid and chloride and sulfate ions as impurities which tend to induce or aid corrosion. Hot mixtures of acetic acid containing over 2% formic acid and at temperatures at or above 250°F may be extremely corrosive towards such highly-resistant alloys as stainless steel 316. Dilute acetic-formic acid solutions at normal distillation temperatures can be advantageously distilled in the more resistant austenitic stainless steels, but even this type of system is made highly corrosion-prone by the presence of chloride and sulfate ions in the crude dilute solutions of acetic acid. The ions tend to destroy the passivating oxide film and attack the exposed metal quite rapidly. For example, stainless steel 304L shows good resistance with 5.6 ppm chloride and 13.0 ppm sulfate, but at 20 and 25 ppm. respectively, high corrosion rates are obtained.

The commercial importance of the lower chain alkanoic acids and industry's need for concentrated, pure forms thereof has brought about the need to reduce production costs. One way this can be done is to more effectively control corrosion of the alloys used in distillation equipment. If corrosion can be controlled, less expensive alloys can be employed in constructing distillation equipment.

The novel process of the present invention provides a significant contribution to that end. It has been discovered that the addition of effective amounts of p-benzoquinone or 1,4-naphthoquinone to the dilute acid solution in the distillation pot, with subsequent normal atmospheric distillation, eliminates or substantially reduces corrosion of stainless steel Types 304 and 316 by corrosive lower chain alkanoic acids. Equally important is the fact that normal atmospheric pressure distillation, i.e., distillation at or near the normal boiling points of the acids, can now be employed with reduced corrosion of the distillation apparatus. The exact mechanism by which the p-benzoquinone and 1,4-naphthoquinone function is, at this time, however, not understood. Nevertheless, practical applications outweigh theoretical considerations. The most immediate commercial importance of the use of this novel corrosion inhibition process is the fact that higher operating pressures and consequently higher distillations temperatures are now made practical, and smaller distillation columns can be employed, with more effective use being made of less expensive metals, for example stainless steel 304 versus Hastelloy.

The process involves the step of introducing an effective amount of the inhibitor into a dilute alkanoic acid solution, wherein the solution can be obtained from any process for manufacturing said acid, or from any other source, and where the desired product is a concentrated and purified form of the acid. The effective amounts of p-benzoquinone or 1,4-naphthoquinone are 10 to 2000 ppm on the basis of weight of acid solution with a preferred range of 100 to 300 ppm. The 2,000 ppm upper limit is dictated by economic considerations and not chemical, and more inhibitor may be used to achieve inhibition. Hydroquinone may also be used along with p-benzoquinone, although such a combination may not be as effective as the p-benzoquinone used alone. The step of heating and vaporizing the acid from solution is the most critical from the standpoint of corrosion, as it is at those high vapor temperatures that the most severe corrosion occurs in the system when the corrosion inhibitor is absent - a condition that is further aggravated by the possible presence of chloride and sulfate ions. With the inhibitor in the system, operating pressures, and thus temperatures can be greatly varied. Pressure can range from about 50 mm to ambient atmospheric pressure, and temperatures can range up to and slightly above the boiling points of the respective acids at the pressure being used. Also, sparging the whole distillation system with air or an oxygen-containing gas is desirable, as this aids in passivating the metal alloy surfaces. The step of recovering the concentrated purified acid is conducted outside the distillation zone. The distillation apparatus is preferably constructed of an austenitic stainless steel, but nothing herein is meant to limit the operativeness of the inhibitors to an austenitic stainless steel system.

The effects of the inhibition of corrosion are examined and measurements made in order to determine the effectiveness of the inhibition. It is important to stress that the general criterion of weight loss is basically an inaccurate measure of corrosion when dealing with metals in which the predominant corrosion attack is that of a pitting nature, as is especially true with the passive alloys, such as the austenitic stainless steels. This type of measurement would show little weight loss because of the small and localized effect of pitting and thus would offer an erroneous picture of the corrosion involved. The very problem of pitting is this very localized effect which often leads to metal perforation - an effect which in a container, for example, may constitute complete failure from the utility standpoint, while leaving the bulk of the metal uncorroded. Thus, determining the nature of the corrosion involved — pitting or uniform corrosion — is most important where corrosion by pitting cannot be tolerated. The results of the examples are given as examination under 45x magnification with measurement of uniform corrosion expressed as inches penetration per year or IPY and notation of those examples in which pitting is observed.

The following examples illustrate the invention:

EXAMPLES

All examples involve static exposure tests.

EXAMPLE I

A 250 ml round bottom flask is charged with concentrated formic acid to which is added a quantity of p-benzoquinone based on weight of formic acid. A corrosion panel is totally immersed in the liquid, the flask is fitted with a thermometer and after sparging with air or nitrogen, is sealed. The flask is heated and the temperature is thermostatically controlled to maintain a bulk liquid temperature in the flask of 95°–100° C. for formic acid. At the end of the test period the corrosion panel is removed from the system, cleaned, weighed and examined under magnification. The results are:

Corrodent: Formic Acid, 90% by weight, 400 gm/Test
Test Panels: Stainless steel 304 and 316
Temperature: 95°–100° C.
Test Conditions: Atmospheric pressure, closed flask, air or nitrogen atmosphere

| Inhibitor | Atmosphere | SS-304 | SS-316 | IPY | Examination at 45× Magnification |
|---|---|---|---|---|---|
| None | Air | X | | 0.052 | C(a) |

-continued

| Inhibitor | Atmosphere | SS-304 | SS-316 | IPY | Examination at 45× Magnification |
|---|---|---|---|---|---|
| None | Air | | X | 0.030 | C(a) |
| None | N₂ | X | — | | P(a) |
| 2000 ppm p-BQ | Air | X | | 0.0003 | NC |
| 2000 ppm p-BQ | Air | | X | 0.0003 | NC |
| 2000 ppm p-BQ | N₂ | X | | 0.0009 | NC |

C = uniform corrosion
P = pitting
NC = no local corrosion
(a) = Purple colored corrosion product on panel surfaces at end of test
p-BQ — p-benzoquinone

EXAMPLE II

A 250 ml round bottom flask is charged with glacial acetic acid to which various concentrations of inhibitor are added on a weight basis of the glacial acetic acid. A corrosion panel is totally immersed in the liquid and provision is made for sparging the liquid with air or nitrogen, the flask also being fitted with a reflux condenser and a thermometer. The flask is heated by means of an oil bath, the temperature is thermostatically controlled to maintain a bulk liquid temperature in the flask of 110°–115° C. for glacial acetic acid. At the end of the test period the corrosion panel is removed from the system, cleaned and weighed. The inches penetration per year (IPY) rate is determined and the specimen examined for corrosion at 45x magnification. The results are:

Corrodent: Glacial Acetic Acid
Test Panel: Stainless Steel 304
Test Conditions: Atmospheric pressure, temperature of 110°–115° C.

| Inhibitor | Sparge | Test Duration, hrs. | IPY | Examination at 45× Magnification |
|---|---|---|---|---|
| None | None 1 | 24 | | Pitting |
| 2000 ppm p-BQ | None 1 | 24 | 0.0025 | No local corrosion |
| 500 ppm p-BQ | None 1 | 26 | 0.0078 | No local corrosion |
| 2000HQ/ 2000 p-BQ | None 1 | 24 | 0.0036 | No local corrosion |
| 2000 ppm HQ | None 1 | 24 | | Pitting |

1 = System open to atmosphere
p-BQ = p-Benzoquinone
HQ = Hydroquinone

EXAMPLE III

The same apparatus is used as in Example II, and the results are:

Corrodent: Glacial Acetic Acid
Test Panel: Stainless Steel 304 and 316
Test Conditions: Atmospheric Pressure, temperature of 110°–115° C.

| Inhibitor | Sparge | Test Duration, hrs. | 304 | 316 |
|---|---|---|---|---|
| None | None 1 | 24 | P | NC |
| 10–100 ppm p-BQ | None 1 | 24 | P | NC |
| 250 ppm p-BQ | None 1 | 24 | OK (IPY=0.011) | NC |
| 500 ppm p-BQ | None 1 | 24 | OK (IPY=0.0077) | NC |
| 2000 ppm p-BQ | None 1 | 24 | OK (IPY=0.0028) | NC |
| 250 ppm HQ | None 1 | 24 | P | NC |
| 2000 ppm HQ | None 1 | 24 | P | NC |
| 10 ppm HQ/ 10 ppm p-BQ | None 1 | 24 | P | NC |
| 100 ppm HQ/ 100 ppm p-BQ | None 1 | 24 | P | NC |
| 250 ppm HQ/ 250 ppm p-BQ | None 1 | 24 | OK (IPY=0.0098) | NC |
| 2000 ppm HQ/ 2000 ppm p-BQ | None 1 | 24 | OK (IPY=0.0040) | NC |

1 = system open to atmosphere
NC = no local corrosion
P = pitting
p-BQ = p-Benzoquinone
HQ = Hydroquinone

EXAMPLE IV

This test is carried out in a controlled atmosphere, the sparge being either air or nitrogen, which is introduced into the same apparatus as that of Example II. The results are:

Corrodent: Glacial Acetic Acid, 400 gm/Test
Test Panel: Stainless 304L
Test Conditions: Controlled Atmosphere, Atmospheric Pressure, Temperature of 110°–115° C.

| Inhibitor | Atmosphere | Test Duration, hrs. | IPY | Examination at 45× Magnification |
|---|---|---|---|---|
| None | Air | 24 | — | P(a) |
| None | N₂ | 24 | — | P(b) |
| 100 ppm p-BQ | Air | 4 | — | P |
| 100 ppm p-BQ | N₂ | 4 | — | P |
| 250 ppm p-BQ | Air | 24 | 0.035 | C |
| 250 ppm p-BQ | N₂ | 4 | 0.035 | C |
| 250 ppm p-BQ | N₂ | 24 | — | P |

-continued

| Inhibitor | Atmosphere | Test Duration, hrs. | IPY | Examination at 45× Magnification |
|---|---|---|---|---|
| 500 ppm p-BQ | Air | 24 | 0.017 | C |
| 500 ppm p-BQ | $N_2$ | 4 | 0.013 | C |
| 500 ppm p-BQ | $N_2$ | 24 | — | P |
| 2000 ppm p-BQ | Air | 24 | 0.0032 | NC |
| 2000 ppm p-BQ | Air | 50 | 0.0023 | NC |
| 2000 ppm p-BQ | Air | 65 | 0.0010 | NC |
| 2000 ppm p-BQ | Air | 90 | 0.0010 | C |
| 2000 ppm p-BQ | $N_2$ | 24 | 0.0079 | C |
| 2000 ppm p-BQ | $N_2$ | 50 | 0.0015 | C |
| 2000 ppm p-BQ | $N_2$ | 65 | — | SP |
| 2000 ppm p-BQ | $N_2$ | 90 | — | SP |

P = pitting  C = uniform corrosion
NC = no local corrosion
p-BQ = p-Benzoquinone
SP = severe pitting
(a) = occurred after about 100 minutes in test
(b) = occurred within one hour of start of test The results in this example show the effects of carrying out a distillation of corrosive alkanoic acid in the absence of oxygen or an oxygen-containing atmosphere. Nitrogen alone, when used as the atmosphere, caused corrosion and even severe pitting over a period of time in the presence of p-benzoquinone. However, those tests carried out in an oxygen-containing atmosphere show no or little corrosion and no pitting over the same period of time and with the same quantity of inhibitor.

EXAMPLE V

The same apparatus as in Example II is used in testing isobutyric acid. The results are:
Corrodent: Isobutyric Acid, concentrated
Test Panel: Stainless Steel 304 and 316
Test Conditions: Atmospheric Pressure, Temperature of 145°–150° C., system open to atmosphere

| Inhibitor | Test Duration, hrs. | SS304 | SS316 | IPY | 45× |
|---|---|---|---|---|---|
| None | 24 | X | — | 0.014 | C |
| None | 24 | — | X | 0.0004 | NC |
| 250 ppm p-BQ | 24 | X | — | — | P |
| 2000 ppm p-BQ | 24 | X | — | 0.0009 | NC |
| 10 HQ ppm/ 10 ppm p-BQ | 24 | X | — | — | P |
| 100 HQ ppm/ 100 ppm p-BQ | 24 | X | — | 0.0011 | NC |
| 250 HQ ppm/ 250 ppm p-BQ | 24 | X | — | 0.0004 | NC |
| 2000 HQ ppm/ 2000 ppm p-BQ | 24 | X | — | 0.0006 | NC |

P = pitting
C = corrosion
NC = no local corrosion
p-BQ = p-Benzoquinone
HQ = Hydroquinone

EXAMPLE VI

A 250 ml round bottom flask is charged with glacial acetic acid to which is added a quantity of inhibitors based on the weight of glacial acetic acid. A corrosion panel is totally immersed in the liquid, the flask is fitted with a thermometer and left open to the atmosphere. The flask is heated and the temperature thermostatically controlled to maintain a bulk liquid temperature in the flask of 110°–115° C. for glacial acetic acid. At the end of the test period, the corrosion panel is removed from the system, cleaned, weighed and examined under magnification. The results are:
Corrodent: Glacial Acetic Acid, 400 gm/Test
Test Panels: Stainless Steel 304
Temperature: 110°–115° C.
Test Conditions: Atmospheric pressure, open flask, air atmosphere

| Inhibitor | Test Duration, hrs. | IPY | Examination at 45× Magnification |
|---|---|---|---|
| None | 24 | — | P |
| 250 ppm HQ | 24 | — | P |
| 250 ppm p-BQ | 24 | 0.021 | C |
| 250 ppm AQ | 24 | — | P |
| 250 ppm NQ | 24 | 0.0051 | NC |
| 2000 ppm NQ | 24 | 0.0029 | NC |
| 250 ppm HQ/ 250 ppm p-BQ | 24 | 0.014 | C |
| 250 ppm HQ/ 250 ppm AQ | 24 | — | P |
| 250 ppm HQ/ | 24 | — | P |

| Inhibitor | Test Duration, hrs. | IPY | Examination at 45× Magnification |
|---|---|---|---|
| 250 ppm NQ | | | |

Note:
1,4-naphthaquinone inhibits corrosion when used alone. However, when used with hydroquinone, pitting occurs, thus effectively preventing the use of hydroquinone in a system using 1,4-naphthoquinone
HQ = Hydroquinone
p-BQ = p-Benzoquinone
AQ = Anthraquinone
NQ = 1,4-Naphthoquinone
P = pitting
C = uniform corrosion
NC = no local corrosion

We claim:

1. In the process for distilling corrosive lower chain alkanoic acids in corrodible metallic distillation apparatus the steps of introducing a crude dilute solution of said corrosive acid into the distillation zone, distilling said acid in the presence of an amount of p-benzoquinone or 1,4-naphthoquinone effective to prevent or reduce to an acceptable limit the corrosion of said metallic distillation apparatus by said corrosive acid, and recovering the purified corrosive acid outside the distillation zone.

2. The process of claim 1, wherein the corrosive acid is selected from the group consisting of formic, acetic, propionic, butyric and isobutyric.

3. The process of claim 2, wherein the corrodible metal is an austenitic stainless steel of composition: C 0.03–08% max., Cr 16–20%, Ni 8–15%, Mo 0–4%, Cb/Ta 0–0.8%, Ti 0–0.4%, the remainder Fe and residual elements.

4. The process of claim 2, wherein the corrodible metal is an austenitic stainless steel of the composition: C .08% max., Cr 18–20%, Ni 8–12%, the remainder Fe and residual elements.

5. The process of claim 2, wherein the corrodible metal is an austenitic stainless steel of the composition: .08% max., Cr 16–18%, Ni 10–14%, Mo 2–3%, the remainder Fe and residual elements.

6. The process of claim 3, where the concentration of p-benzoquinone is 10 to 3000 ppm based on the weight of crude acid solution.

7. The process of claim 3, where and the concentration of p-benzoquinone is 100 to 300 ppm based on the weight of crude acid solution.

8. The process of claim 3, wherein the corrosion inhibitor is 1,4-naphthoquinone in a concentration of 10 to 3000 ppm based on the weight of crude acid solution.

9. The process of claim 3, wherein the corrosion inhibitor is 1,4-naphthoquinone in a concentration of 100 to 300 ppm based on the weight of crude acid solution.

10. The process of claim 7, wherein the corrosive acid is formic acid.

11. The process of claim 7, wherein the corrosive acid is acetic acid.

12. The process of claim 7, wherein the corrosive acid is propionic acid.

13. The process of claim 7, wherein the corrosive acid is butyric acid.

14. The process of claim 7, wherein the corrosive acid is isobutyric acid.

15. The process of claim 9, wherein the corrosive acid is formic acid.

16. The process of claim 9, wherein the corrosive acid is acetic acid.

17. The process of claim 9, wherein the corrosive acid is propionic acid.

18. The process of claim 9, wherein the corrosive acid is butyric acid.

19. The process of claim 9, wherein the corrosive acid is isobutyric acid.

20. The process of claim 1, wherein the distillation is carried out at or near ambient atmospheric pressure.

21. The process of claim 7, wherein the distillation is carried out in an oxygen-containing distillation system.

* * * * *